US012768778B2

(12) United States Patent
Pejic et al.

(10) Patent No.: US 12,768,778 B2
(45) Date of Patent: Oct. 20, 2026

(54) FRAME WITH SENSORS FOR SAMPLING HONEYCOMB CONTENT BASED ON THE METHOD OF ABSORPTION SPECTROSCOPY

(71) Applicant: BEEHOLD D.O.O. NIS, Nis (RS)

(72) Inventors: Petar Pejic, Nis (RS); Jelena Pejic, Nis (RS); Mihajlo Milovanovic, Sokobanja (RS)

(73) Assignee: BEEHOLD D.O.O. NIS, Nis (RS)

( * ) Notice: Subject to any disclaimer, the term of this patent is extended or adjusted under 35 U.S.C. 154(b) by 84 days.

(21) Appl. No.: 18/718,452

(22) PCT Filed: Dec. 14, 2022

(86) PCT No.: PCT/RS2022/000017
§ 371 (c)(1),
(2) Date: Jun. 11, 2024

(87) PCT Pub. No.: WO2023/113633
PCT Pub. Date: Jun. 22, 2023

(65) Prior Publication Data

US 2025/0052669 A1 Feb. 13, 2025

(30) Foreign Application Priority Data

Dec. 14, 2021 (RS) ................................. P-2021/1537

(51) Int. Cl.
*G01N 21/31* (2006.01)
*A01K 29/00* (2006.01)
(Continued)

(52) U.S. Cl.
CPC ........... *G01N 21/31* (2013.01); *A01K 29/005* (2013.01); *A01K 47/02* (2013.01); *A01K 47/06* (2013.01); *G01N 33/02* (2013.01)

(58) Field of Classification Search
CPC ...... G01N 21/31; G01N 33/02; A01K 29/005; A01K 47/02; A01K 47/06; A01K 47/04
(Continued)

(56) References Cited

U.S. PATENT DOCUMENTS

2012/0237415 A1* 9/2012 Ramos ..................... B01J 8/008
29/890
2013/0266501 A1* 10/2013 He ......................... B82Y 40/00
977/734

(Continued)

FOREIGN PATENT DOCUMENTS

RS 2126204 C1 2/1999
RS 1705 U1 4/2021

OTHER PUBLICATIONS

Absorption spectroscopy , Dec. 1, 2021, Wikipedia, https://en.wikipedia.org/wiki/Absorption_spectroscopy (Last accessed : Jun. 3, 2024).

*Primary Examiner* — Md M Rahman
(74) *Attorney, Agent, or Firm* — Jose Cherson Weissbrot

(57) ABSTRACT

The frame (1) with sensors (3) for sampling the contents of the honeycomb based on the method of absorption spectroscopy, includes a honeycomb foundation (2) within which are sensors (3) connected by a parallel bundle of wires (4) to a central microprocessor unit with memory (5) which is connected to the power supply unit (6) and the communication subsystem (7) so that the behavior of the bees and the usual manipulation of the beekeepers are preserved. The system refers to the field of application of electrical engineering for monitoring biological systems, and specifically to sensory monitoring of bee colonies by determining the content of honeycombs within the brood chamber of the frame. The system finds application in beekeeping for non-invasive remote control of bee colonies in the subject hive.

2 Claims, 3 Drawing Sheets

Figure 1:
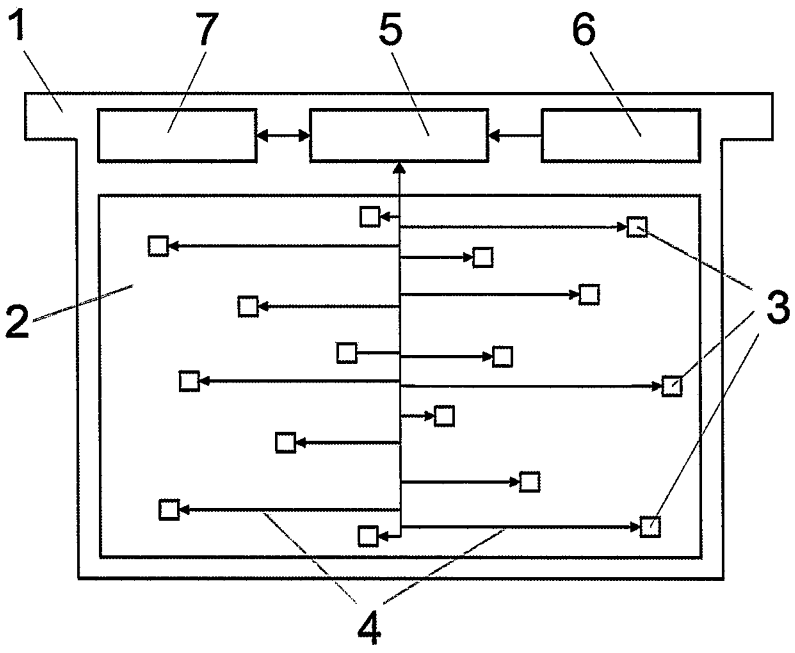

(51) Int. Cl.

| | |
|---|---|
| ***A01K 47/02*** | (2006.01) |
| ***A01K 47/06*** | (2006.01) |
| ***G01N 33/02*** | (2006.01) |

(58) Field of Classification Search
USPC ........................................................ 356/326
See application file for complete search history.

(56) References Cited

U.S. PATENT DOCUMENTS

2017/0167977 A1* 6/2017 Rivera .................. G01N 21/64
2021/0307301 A1 10/2021 Zmyslony et al.

* cited by examiner

FRAME WITH SENSORS FOR SAMPLING HONEYCOMB CONTENT BASED ON THE METHOD OF ABSORPTION SPECTROSCOPY

TECHNICAL FIELD TO WHICH THE INVENTION RELATES

The invention relates to the field of application of electrical engineering for the monitoring of biological systems, and specifically to the sensor monitoring of the bee colony by determining the content of the honeycomb inside the hive frame.

According to the International Classification of Patents, the subject of the invention can be classified into the following classes:

A01K47/02 (2006 January)—construction or arrangement of honeycomb frames.

A01K 47/06 (2006 January)—other details of the hive, e.g. ventilation devices, hive entrances, safety devices, partitions or exits for bees.

TECHNICAL PROBLEM

The technical problem solved by the respective invention consists in the following: how to non-invasively sample the contents of the comb inside the hive frame without opening the hive and manual visual inspection by the beekeeper?

STATE OF ART

The traditional procedure of monitoring the bee colony involves opening the hive, pulling out each frame and visual inspection by the beekeeper 5-15 times a year. In order to carry out this procedure, the beekeeper need to be physically present, which in some cases involves a journey of hundreds of kilometers. The procedure also involves opening the hive and removing the frames, which disrupts the internal ecosystem of the bee colony.

Scientific research in the field of digital solutions for monitoring the state of the bee colony includes:

analysis of changes in society's weight (J. Flores, et al., Effect of the climate change on honey bee colonies in a temperate Mediterranean zone assessed through remote hive weight monitoring system in conjunction with exhaustive colonies assessment, Science of the Total Environment 653, 2019.);

sound monitoring inside the hive (N. Perez, et al., Continuous monitoring of beehives' sound for environmental pollution control, Ecological Engineering 90, 2016.);

temperature monitoring inside the hive (K. Kridi, et al., Application of wireless sensor networks for beehive monitoring and in-hive thermal patterns detection, Computers and Electronics in Agriculture 127, 2016.), (D. Kridi, et al., Application of wireless sensor networks for beehive monitoring and in-hive thermal patterns detection, Computers & Electronics in Agriculture, 2016.), (Small Patent: MII-2019/0045, Republic of Serbia);

application of gas sensors (A. Szczurek, Detecting varroosis using a gas sensor system as a way to face the environmental threat, Science of the Total Environment 722, 2020.);

monitoring the health of the bee colony by analyzing several parameters: CO2, O2, harmful gases, temperature, humidity (F. Murphy, et al., b+WSN: Smart beehive with preliminary decision tree analysis for agriculture and honey bee health monitoring Computers and Electronics in Agriculture 124, 2016.).

Commercially available bee colony monitoring solutions offer different combinations of sensors for: weight measurement, temperature measurement, air humidity measurement and sound analysis inside the hive:

Apis Protect (www.apisprotect.com);

BeeHero (www.beehero.io);

OSBeehives (www.osbeehives.com);

Pollenity (www.pollenity.com);

Arnia (www.arnia.co.uk).

However, all the above solutions from practice as well as scientific research do not offer the possibility of detecting the contents of the honeycomb inside the frame without opening the hive and manual visual inspection of the beekeeper.

PRESENTATION OF THE ESSENCE OF THE INVENTION

The essence of the invention consists in the selection of a suitable operating principle of the sensor for sampling the contents of the honeycomb, which is based on the method of absorption spectroscopy, as well as in the selection of a suitable position and arrangement of the sensor within the honeycomb base of the frame. The absorption spectroscopy method measures the absorption of radiation caused by interaction with the sample. With this method, it is possible to determine the composition of the comb: empty comb, comb with honey, comb with pollen or comb with bee brood. Sampling of the contents of the comb is not conditioned by the physical presence of the beekeeper, time of day or weather conditions as in the traditional procedure of monitoring the bee colony. The time interval of sampling the contents of the honeycomb is negligible compared to the time required for the contents of the honeycomb to change, so that the resulting content can be considered to be instantaneous.

A BRIEF DESCRIPTION OF THE DRAWINGS

The invention is described on the example of execution shown in the drawing in which:

FIG. 1—shows a simplified assembly view of the invention and its structure

Figure 2:
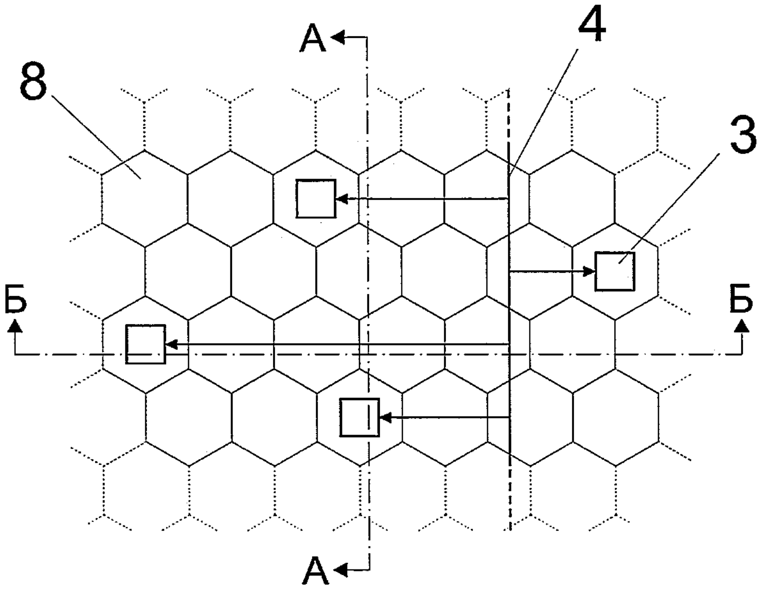

FIG. 2—shows the layout of the honeycomb base with sensors

Figure 3:
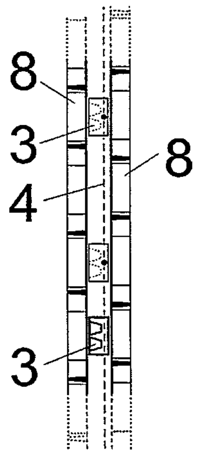

FIG. 3—shows the A-A cross section of the honeycomb base with sensors

Figure 4:
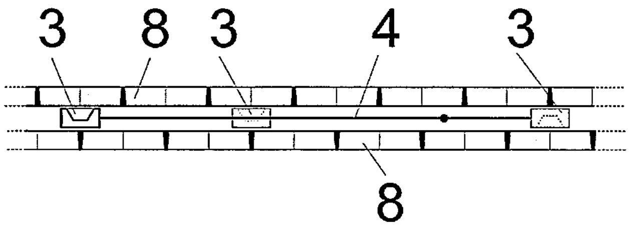

FIG. 4—shows a cross-section of the B-B honeycomb base with sensors

Figure 5:
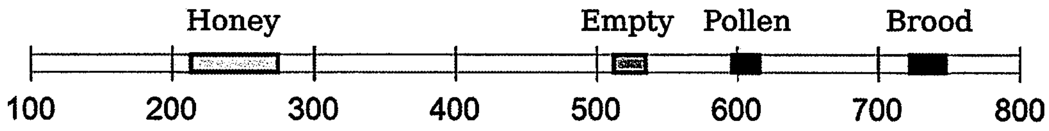
Figure 6:
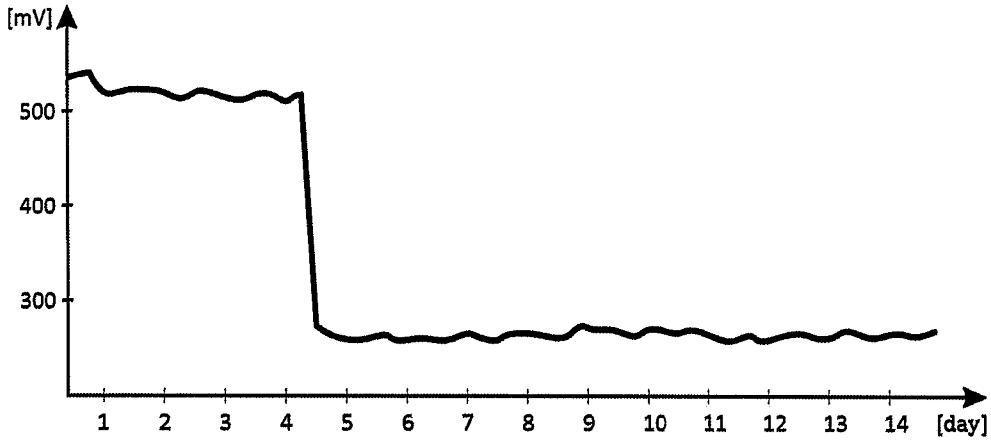
Figure 7:
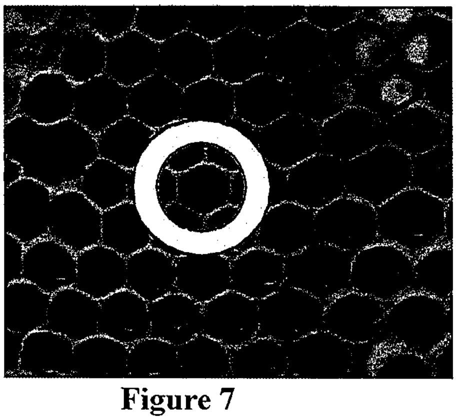
Figure 8:
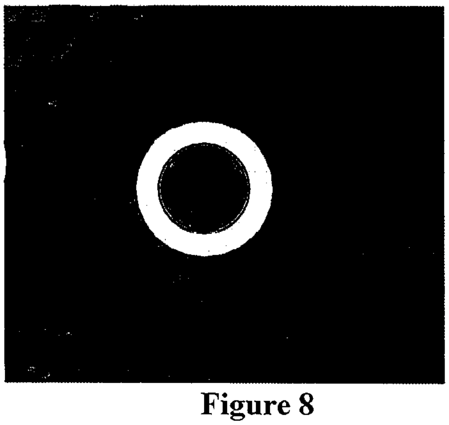

FIG. 5—shows the distribution of the amount of reflected light in relation to the content of the honeycomb FIG. 6—shows the results of sampling one honeycomb using the absorption spectroscopy method over a period of 15 days FIG. 7—shows the appearance of the honeycomb on the fourth day of testing the invention FIG. 8—shows the appearance of the honeycomb on the sixth day of testing the invention

DETAILED DESCRIPTION OF THE INVENTION

Before setting forth the details of the invention, it is important to understand and emphasize that the respective invention is not limited to the details of construction illustrated and described below. The terms used in the description of the invention serve to understand the invention and not to limit it.

An example of the implementation of a frame with sensors for sampling the contents of the honeycomb is shown in FIG. 1. The basic components of the frame 1 are the honeycomb base 2, the central microprocessor unit with memory 5, the power supply unit 6 and the communication subsystem 7, which enables two-way networking with the global computer network, via one or more different links. The constituent parts of frame 1 are incorporated into the hive system so that the standard dimensions and functions of individual hive parts are preserved. The honeycomb base 2 includes sensors for sampling the contents of the honeycomb 3 and a wire bus 4 for connecting to the central microprocessor unit with the memory 5. The central microprocessor unit with the memory 5 reads the content of the honeycomb using the sensor 3 inside the honeycomb base 2 in a time interval that is negligible compared to the time required for the contents of the honeycomb to change. The read values of the content are stored in memory, and can be at an arbitrary destination on the global computer network.

Given that the system in question deals with the application of technology to a biological system, the technical part must meet the conditions of biocompatibility and non-invasiveness. With the intention that the integration into the technical system preserves the existing biological system, frame 1 and honeycomb base 2 are integrated in such a way as to preserve the structure and functionality of the beehive. FIGS. 2, 3 and 4 show the integration of the sensor 3 and the wire bus 4, which is carried out through the honeycomb base 2 in three projections, from above, on the section A-A and on the section B-B respectively. The constituent parts of the honeycomb base 2 are the sensors for sampling the contents of the comb 3 and the wire bus 4 placed between two cover plates 8. The cover plates 8 are compatible in length and width with the honeycomb bases of the hive systems for rational beekeeping, while their thickness is minimal to ensure the penetration of air sensor 3 and had sufficient strength to carry the weight of the honeycomb. The cover plates 8 are made of material that allows the penetration of the air of the sensor 3 and does not harm the bees and bee products with which it is in contact. The component parts of the honeycomb base 2 are integrated into the hive system so that the standard dimensions and functions of individual parts of the hive are preserved.

The working principle of the invention is based on the method of absorption spectroscopy. Sampling of the contents of the honeycomb is performed with a photoelectric sensor 3 that emits an infrared light beam and measures the reflection of the rays from the contents of the honeycomb. The amount of reflected light determines the content of the honeycomb. The advantages of this method consist in the fact that the sampling is not conditioned by the physical presence of the beekeeper, the time of day or weather conditions as in the traditional procedure of monitoring the bee colony. All the sensors 3 within the frame 1 can be read in a time interval that is negligible compared to the time required for the content of the honeycomb to change, so that the resulting content can be considered instantaneous.

The proposed invention is realized by DB frame 1, TR8307/L24/TR8 sensor 3 with infra-red diode and silicon phototransistor, placed inside honeycomb base 2 with cover plate 8 made of Polylactide, Arduino Nano central microprocessor unit with memory 5 and Esp8266 WiFi communication module 7. The proposed invention was experimentally tested in laboratory conditions by measuring the amount of reflected light for: empty honeycomb, honeycomb with honey, honeycomb with pollen and honeycomb with bee brood. The test results are shown in FIG. 5. The test was carried out for different types of pollen and honey (mountain, meadow, acacia and sunflower) and different amounts starting from a fifth of a full comb to a completely full comb. The test was also carried out for bee brood in various stages of development, from larva to adult bee.

Sampling of the honeycomb content using the absorption spectroscopy method was confirmed in real conditions by comparing the measurement results and manual visual inspection of the frame 1 placed inside the hive. FIG. 6 shows the results of sampling the contents of one honeycomb, performed at equal time intervals of 6 hours during 15 days. The measurement results and visual inspection confirm that honey was collected in the comb on the fifth day. FIG. 7 shows that the sampled comb is empty on the fourth day, while FIG. 8 shows that there is honey in the same comb on the sixth day. This illustrates the sampling of honeycomb contents by the method of absorption spectroscopy.

METHOD OF INDUSTRIAL OR OTHER APPLICATION OF THE INVENTION

The proposed solution based on the absorption spectroscopy method can be used for sampling the contents of honeycomb and non-invasive remote monitoring of the bee colony. The invention represents a replacement for the traditional manual monitoring of the bee colony by visual inspection of the frames, without the need for physical presence in the apiary, it enables a much faster inspection of the bee colony in all weather conditions and during all seasons. The invention can also be used as a data collection unit in the process of wider monitoring of beekeeping at levels higher than the level of the bee colony, the apiary, the local level, the state level, the regional level and the global level.

The invention claimed is:

1. A frame (1) with a plurality of photoelectric sensors (3) for sampling a contents of a honeycomb, based on absorption spectroscopy, the frame (1) comprising:

a honeycomb base (2) comprising two cover plates (8), the plurality of photoelectric sensors (3), and a wire bus (4), wherein the plurality of photoelectric sensors (3) and the wire bus (4) are disposed between the two cover plates (8);

a central microprocessor with a memory (5) connected to the plurality of photoelectric sensors (3) by the wire bus (4);

a power supply unit (6) connected to the central microprocessor with the memory (5); and a communication subsystem (7) connected to the central microprocessor with the memory (5), wherein each photoelectric sensor (3) comprises an infrared diode and a silicon phototransistor, the infrared diode being arranged to emit an infrared light beam toward the contents of the honeycomb, and the silicon phototransistor being arranged to measure reflected light from the contents of the honeycomb, and wherein the central microprocessor with the memory (5) determines, based on an amount of the reflected light measured by the plurality of photoelectric sensors (3), whether the contents of the honeycomb comprise empty honeycomb, honey, pollen, or bee brood.

2. The frame (1) according to claim 1, wherein the frame (1) and the honeycomb base (2) are of the same dimensions as the frame and the honeycomb base of a beehive system for rational beekeeping.

* * * * *